(12) United States Patent
Abedin et al.

(10) Patent No.: US 11,678,825 B2
(45) Date of Patent: Jun. 20, 2023

(54) METHODS AND SYSTEMS FOR COLLECTING SAMPLES IN A PHOTOPHERESIS PROCEDURE

(71) Applicant: Fenwal, Inc., Lake Zurich, IL (US)

(72) Inventors: Tanima Jahan Abedin, Chicago, IL (US); Nicole F. Young, Antioch, IL (US); Lan T. Nguyen, Vernon Hills, IL (US); Zahra R. Ali, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 578 days.

(21) Appl. No.: 16/590,903

(22) Filed: Oct. 2, 2019

(65) Prior Publication Data

US 2020/0107765 A1    Apr. 9, 2020

Related U.S. Application Data

(60) Provisional application No. 62/741,356, filed on Oct. 4, 2018.

(51) Int. Cl.
*A61B 5/00* (2006.01)
*A61B 5/15* (2006.01)
*A61M 1/36* (2006.01)

(52) U.S. Cl.
CPC ..... *A61B 5/150992* (2013.01); *A61M 1/3683* (2014.02)

(58) Field of Classification Search
CPC .......... A61B 5/150992; A61M 1/3683; A61M 1/0236
USPC ........................................................ 600/581
See application file for complete search history.

(56) References Cited

U.S. PATENT DOCUMENTS

| | | | |
|---|---|---|---|
| 4,321,919 A | | 3/1982 | Edelson |
| 5,360,542 A | * | 11/1994 | Williamson, IV .. A61M 1/3696 210/512.1 |
| 5,370,802 A | * | 12/1994 | Brown ................. A61M 1/308 210/194 |
| 6,027,657 A | * | 2/2000 | Min .................... A61M 1/3603 210/744 |
| 6,592,613 B1 | | 7/2003 | Ishida et al. |
| 7,433,030 B2 | | 10/2008 | Waldo et al. |
| 7,479,123 B2 | | 1/2009 | Briggs |
| 7,824,343 B2 | | 11/2010 | Mathias et al. |
| 9,399,093 B2 | | 7/2016 | Min et al. |
| 10,088,492 B2 | | 10/2018 | Wegener et al. |
| 10,172,995 B2 | | 1/2019 | Radwanski et al. |
| 10,213,544 B2 | | 2/2019 | Radwanski |
| 10,363,355 B2 | | 7/2019 | Prendergast et al. |
| 10,434,239 B1 | * | 10/2019 | Briggs ............... A61M 1/3681 |
| 10,434,240 B2 | | 10/2019 | Abedin et al. |
| 10,518,020 B2 | | 12/2019 | Min et al. |
| 10,556,053 B2 | | 2/2020 | Abedin et al. |
| 10,751,433 B2 | | 8/2020 | Crawley et al. |
| 10,886,022 B2 | | 1/2021 | Ali et al. |
| 10,980,933 B2 | | 4/2021 | Prendergast et al. |
| 11,311,823 B2 | | 4/2022 | Kusters et al. |

(Continued)

OTHER PUBLICATIONS

Extended European Search Report for European Application No. 19201103.9 dated Feb. 13, 2020.

*Primary Examiner* — May A Abouelela
(74) *Attorney, Agent, or Firm* — Cook Alex Ltd.

(57) ABSTRACT

Methods and systems for sampling blood components in a photopheresis procedure are disclosed. The methods include collecting samples at selected times during a photopheresis procedure.

6 Claims, 6 Drawing Sheets

(56) References Cited

U.S. PATENT DOCUMENTS

| | | |
|---|---|---|
| 11,318,239 B2 | 5/2022 | Ali et al. |
| 2003/0222029 A1* | 12/2003 | Muller .............. A61M 1/3696 210/85 |
| 2007/0060872 A1* | 3/2007 | Hall .................. A61B 5/155 600/581 |
| 2007/0083143 A1* | 4/2007 | Braig .............. A61B 5/150755 604/6.08 |
| 2009/0048535 A1* | 2/2009 | Robinson .......... A61B 5/15003 600/581 |
| 2011/0009720 A1* | 1/2011 | Kunjan ............ A61B 5/14532 600/581 |
| 2012/0289926 A1* | 11/2012 | Hirabuki ........... A61M 1/0236 604/406 |
| 2013/0101464 A1* | 4/2013 | Smyczynski .......... A61M 1/32 422/44 |
| 2013/0197419 A1* | 8/2013 | Min .................. A61M 1/3693 422/44 |
| 2014/0263529 A1 | 9/2014 | Stonig |
| 2015/0196706 A1* | 7/2015 | Radwanski ......... A61M 1/3696 422/44 |
| 2015/0265202 A1* | 9/2015 | Nakata ............... A61B 1/015 600/581 |
| 2015/0343060 A1* | 12/2015 | Kovar ............... A61K 51/082 210/695 |
| 2016/0114095 A1* | 4/2016 | Radwanski ......... A61K 35/15 435/2 |
| 2016/0177262 A1 | 6/2016 | Wegener et al. |
| 2016/0195555 A1* | 7/2016 | Wegener ........... A61M 1/3683 435/39 |
| 2017/0021042 A1 | 1/2017 | Dodd et al. |
| 2017/0028121 A1* | 2/2017 | Manzella .......... A61M 1/3683 |
| 2017/0049951 A1* | 2/2017 | Abedin ............. A61M 1/3693 |
| 2017/0197023 A1 | 7/2017 | Radwanski et al. |
| 2018/0078694 A1 | 3/2018 | Abedin et al. |
| 2018/0154066 A1* | 6/2018 | Briggs ............. A61M 1/3683 |
| 2018/0214626 A1* | 8/2018 | Abedin ............. B04B 5/0442 |
| 2019/0015578 A1* | 1/2019 | Smyczynski .......... A61M 1/32 |
| 2019/0085289 A1* | 3/2019 | Greenman .......... A61K 41/17 |
| 2019/0099544 A1* | 4/2019 | Abedin ............. A61M 1/3644 |
| 2019/0224494 A1 | 7/2019 | Radwanski et al. |
| 2019/0344008 A1* | 11/2019 | Igarashi ........... A61M 1/3683 |
| 2020/0222620 A1 | 7/2020 | Ali et al. |
| 2020/0297914 A1 | 9/2020 | Radwanski et al. |

* cited by examiner

METHODS AND SYSTEMS FOR COLLECTING SAMPLES IN A PHOTOPHERESIS PROCEDURE

CROSS-REFERENCE TO RELATED APPLICATION

This application claims the benefit of U.S. Provisional Patent Application Ser. No. 62/741,356, filed on Oct. 4, 2018, the disclosure of which is incorporated herein by reference in its entirety.

FIELD OF THE DISCLOSURE

The present disclosure is directed to the processing and collection of blood and its components in a photopheresis procedure. More particularly, the present disclosure is directed to methods and systems for collecting samples of a blood component at selected times in a photopheresis procedure.

BACKGROUND

Whole blood can be separated into its constituent components (cellular or liquid), and the desired component can be separated so that it can be administered to a patient in need of that particular component. For example, mononuclear cells (MNCs), primarily lymphocytes and monocytes, can be removed from the whole blood of a patient, collected, and subjected to photodynamic therapy in a procedure commonly referred to as extracorporeal photopheresis, or ECP. In ECP, MNCs are treated with a photoactivating or photosensitizing agent (e.g., 8-methoxypsoralen (8-MOP)), subsequently irradiated with specified wavelengths of light to achieve a desired effect, and returned to the patient for the treatment of various blood diseases to, e.g., eliminate immunogenicity in cells, inactivate or kill selected cells, inactivate viruses or bacteria, or activate desirable immune responses. If delivered in the right dosage, the combination of a photoactivating agent and light causes an apoptotic response in the treated MNCs. This response is the desired treatment for conditions such as Cutaneous T-Cell lymphoma (CTCL), Acute and chronic Graft versus host disease (GvHD), and Heart and Lung transplant rejection.

In one example of an ECP procedure, blood is withdrawn from the patient and the mononuclear cells are separated (typically by centrifugation) from the remainder of the other whole blood components. The separated mononuclear cells are combined with a selected dose of 8-MOP or other photoactivating agent and subjected to light (typically UV-A) to activate the molecules of the photoactivating agent. The light crosslinks 8-MOP to DNA strands inside the cell and on the cell wall of the exposed MNCs, eventually causing cell apoptosis. The fluid with the altered MNCs is reinfused back into the patient to induce an immune system response.

The procedure is carried out using a disposable fluid circuit, i.e., a "kit," that includes devices for accessing the vascular system of the patient (e.g., venipuncture needles), tubing that defines flow paths for conveying fluid to and from the patient to a separation chamber and a treatment container, and solution or storage containers. Examples of a photopheresis methods and systems of the type described above are set forth in U.S. Pat. No. 9,399,093, U.S. Patent Application Publication No. US 2014/037049 and U.S. Patent Application Publication No. US 2018/0078694 the contents of which are incorporated herein by reference in their entireties.

At present, there remains much speculation regarding the mechanisms of action of ECP. Accordingly, efforts to study the progression of the collected MNCs after irradiation are ongoing. To facilitate this effort, it would be desirable to have a method by which samples can be taken from the collected MNCs and the treated MNCs without the risk of contamination or dilution from other components in the disposable kit. The ability to collect samples in a sterile manner before and after irradiation/treatment may allow for a more complete understanding of the effectiveness and progression of ECP treatment on the MNCs. Thus, the disposable configuration should be such that it allows for such sample retrieval without the risks of contamination. The disposable configuration should also allow for flexibility of what samples to collect and when, and whether any samples should be collected at all.

SUMMARY

In one embodiment, the present disclosure is directed to a method for collecting blood samples in a photopheresis procedure. The method includes programming a photopheresis system for pausing a photopheresis procedure to allow for the collection of blood sample at selected time intervals. The method also includes collecting a first sample of a blood component to be treated by radiation at a time prior to irradiation of the collected blood component, continuing with said photopheresis procedure and collecting a sample of a blood component that has been treated by radiation. The selected times may include the time when the desired blood component has been collected, the time after addition of the photoactivating agent to the collected blood component and the time after the blood component has been treated with radiation. Additional samples may be collected at other times as well. The photopheresis system may prompt the operator when a sample is to be drawn.

DETAILED DESCRIPTION OF THE EMBODIMENTS

Figure 1:
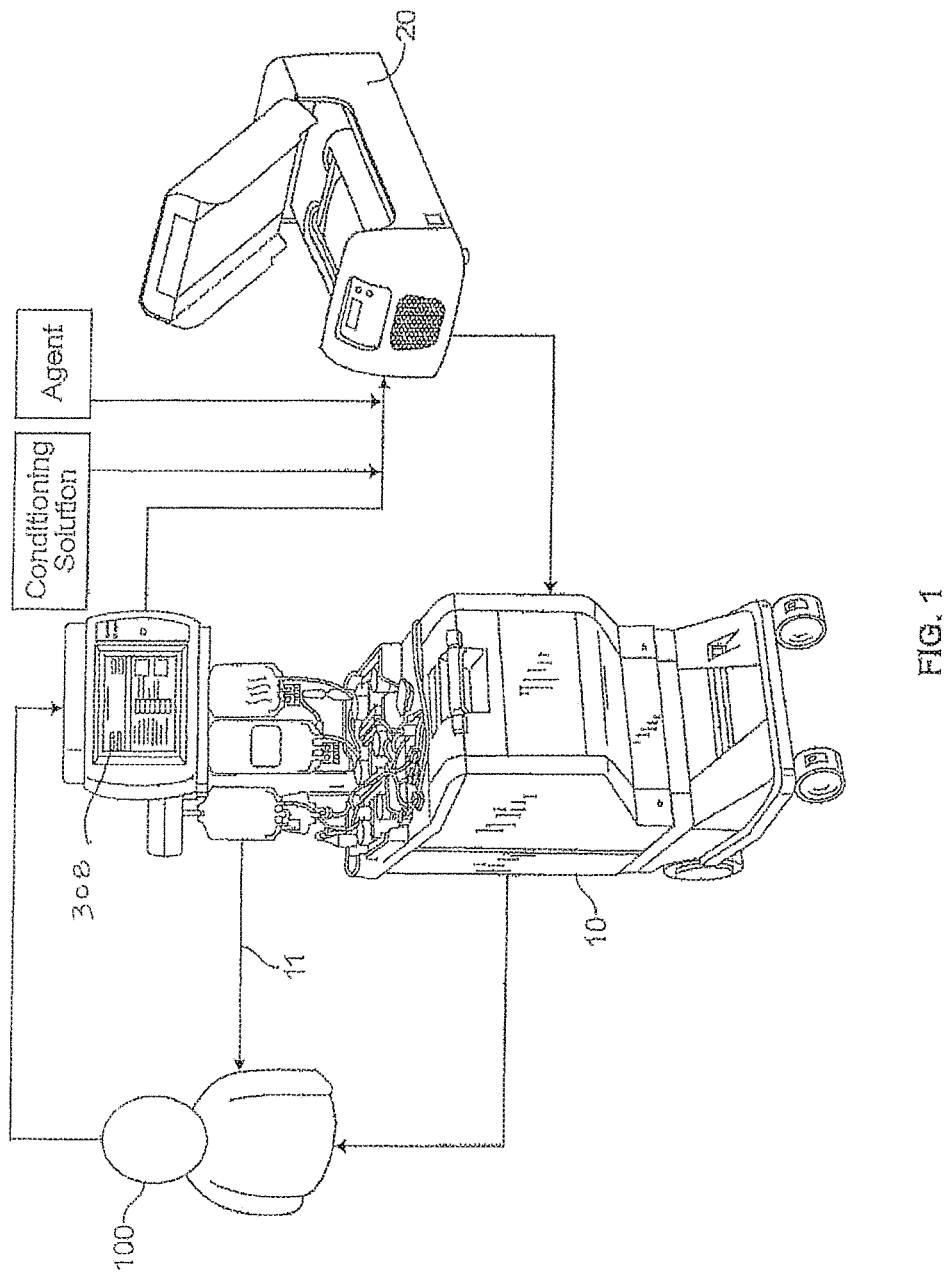
FIG. 1 is a diagram of the system and method for processing a mononuclear cell product in accordance with the present disclosure.

Turning now to the Figures, FIG. 1 diagrammatically shows one example of a system for carrying out ECP and the flow of fluid in the method described herein. In accordance with the present disclosure, the system includes a reusable separation unit or separator 10 and a treatment or irradiation unit 20. In one embodiment, irradiation unit 20 is independent and housed separately from separator 10. Although separately housed and shown as independent, stand-alone devices, it is preferable that separator 10 and irradiation device 20 be located adjacent to each other. While FIG. 1 shows a preferred embodiment of the individual separation and irradiation units, it will be appreciated that the methods described herein may also be used with devices having integrated separation and irradiation components housed in one device.

As generally shown in FIG. 1, whole blood is withdrawn from the patient 100 and introduced into the separator 10 where the whole blood is separated to provide a target cell population. More particularly, whole blood is withdrawn from the patient through venipuncture needle 82 (FIG. 3) and introduced into the separation chamber of separation container 12 carried within and/or mounted on a centrifuge device of separator 10. Within the separator 10, the target cell population is separated from other components. In a preferred embodiment in accordance with the present disclosure, the target cell population is the patient's mononuclear cells (MNC). Other components separated from the whole blood in this initial separation, such as red blood cells, plasma and platelets, may be returned to the patient or collected in pre-attached containers of the blood processing set, as shown by line 11. The collection of mononuclear cells is more specifically described in U.S. Pat. No. 6,027,657, the contents of which is incorporated herein by reference.

The separated target cell population, e.g., mononuclear cells with residual red blood cells and plasma, is then prepared for treatment and irradiation in reusable treatment component or irradiation unit 20. In accordance with the present disclosure, effective treatment of the mononuclear cells with ultraviolet light requires that the collected mononuclear cells be provided in a suspension having a suitable hematocrit, i.e., a certain (low) concentration of red blood cells. Specifically, the hematocrit level in the MNC suspension to be treated affects the amount of UV light that the MNC are exposed to as the red blood cells in the MNC suspension will block at least a portion the UV light from reaching the targeted MNCs. The hematocrit level of the MNC product to be treated may be adjusted by diluting the collected MNC product with plasma and/or saline, as described in U.S. Pat. No. 9,399,093 and U.S. Patent Application Publication No. US2014/0370491, both previously incorporated by reference. After treatment/irradiation, the treated component is returned to the patient 100 (as shown in FIG. 1) under the direction of controller 300 (of the separator 10), discussed in greater detail below.

Turning now, more specifically, to one embodiment of the reusable hardware units and disposable fluid circuit components of the system, devices/separators 10 useful in the collection (and washing) of mononuclear cells include the Amicus® Separator made and sold by Fresenius-Kabi USA, of Lake Zurich, Ill. As noted previously, mononuclear cell collections using a device such as the Amicus® are described in greater detail in U.S. Pat. No. 6,027,657, previously incorporated by reference herein in its entirety.

Figure 2:
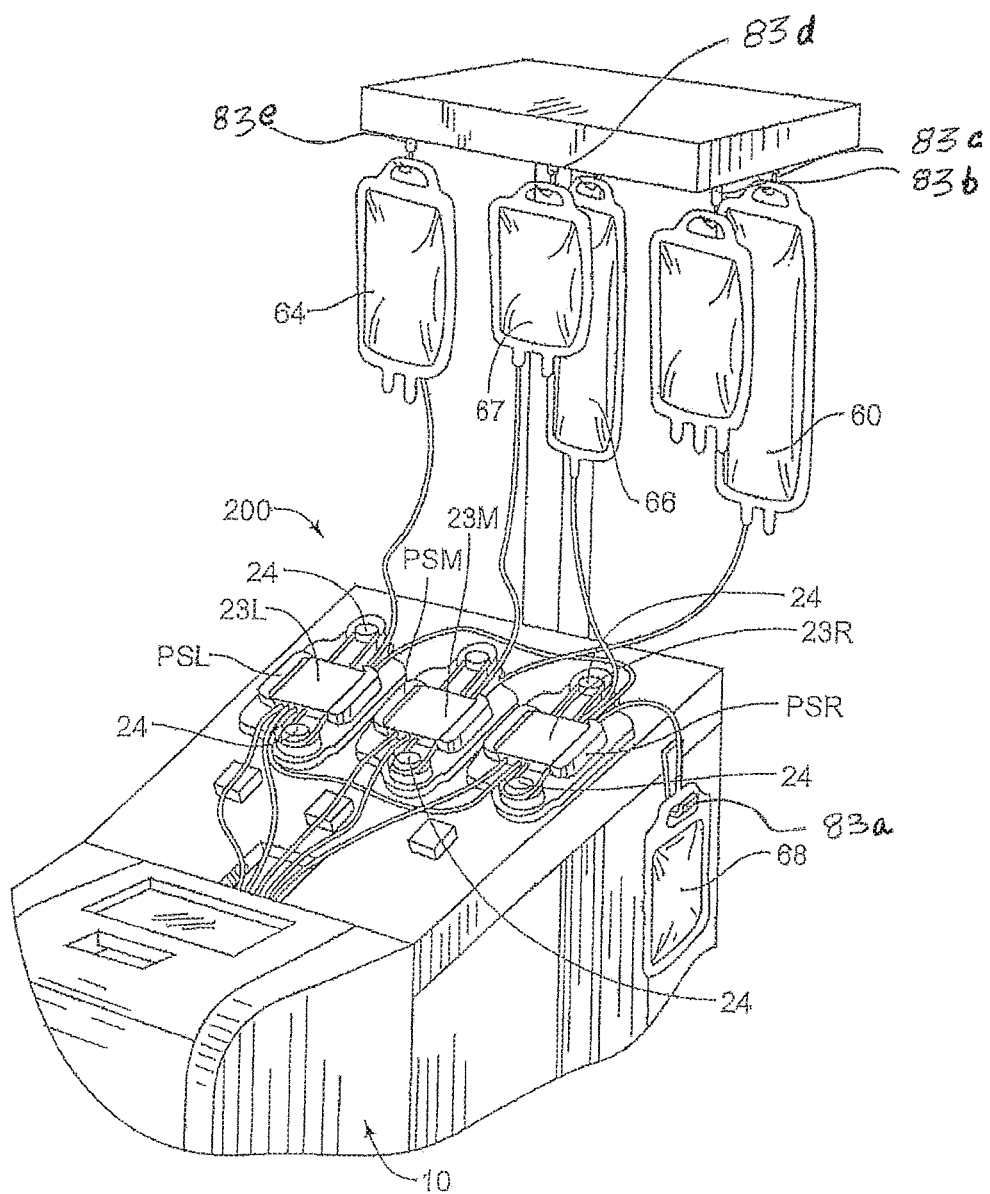
FIG. 2 is a partial perspective view of the front panel of a multifunctional apheresis separator useful in the methods and systems described herein with a portion of the disposable fluid circuit mounted thereon.
Figure 3:
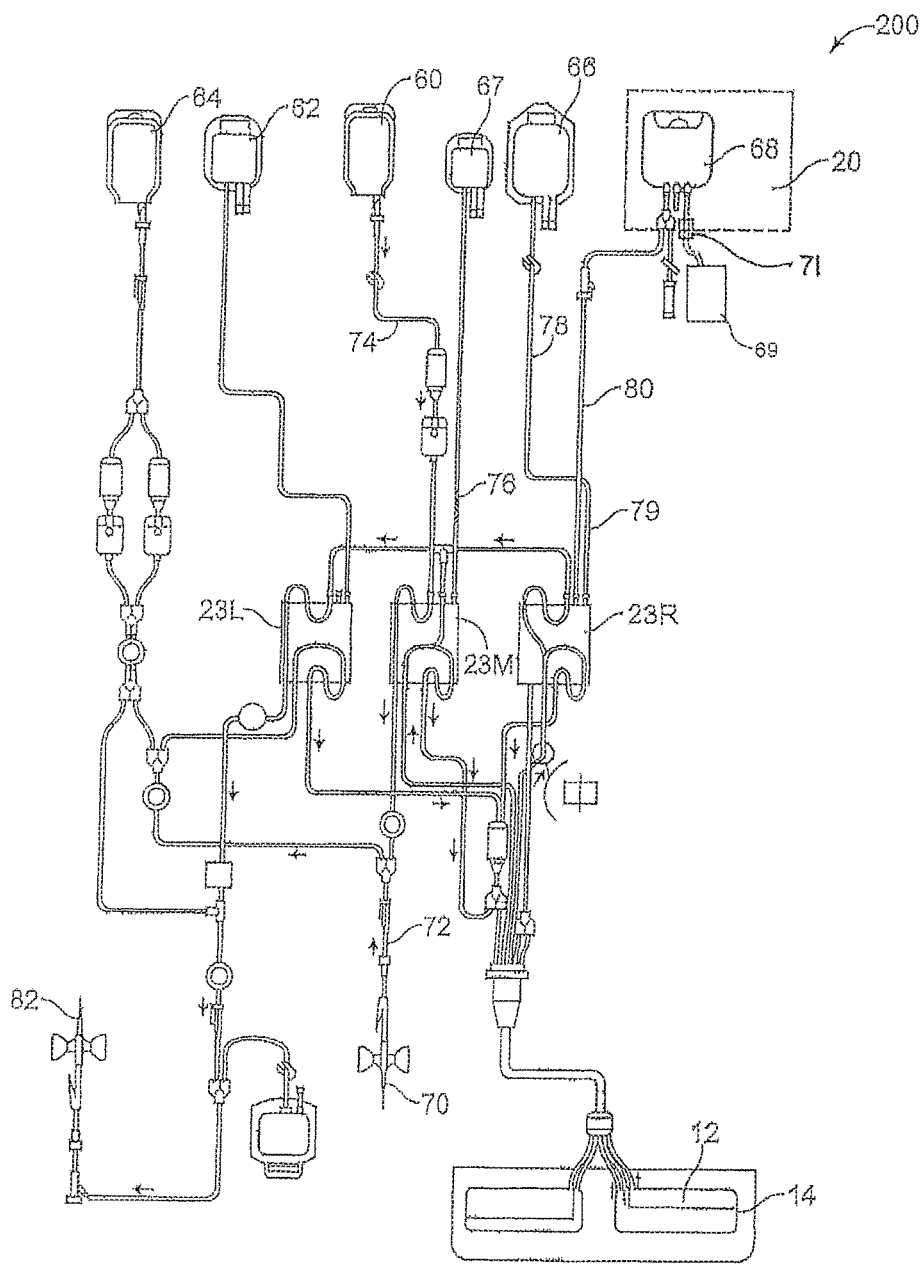
FIG. 3 is a diagram of one embodiment of a disposable fluid circuit suitable for use with the system described herein.
Figure 4:
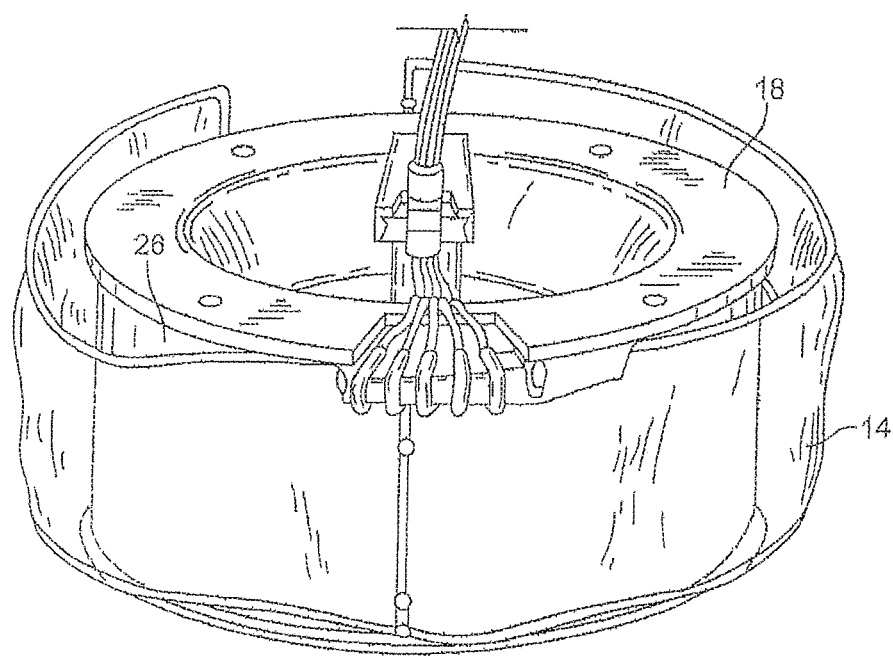
FIG. 4 is a perspective view of a container with separation chamber of the fluid circuit used with a separator.

Briefly, FIG. 2 shows a representative blood centrifuge device/separator 10 with fluid circuit 200 mounted thereon. The fluid circuit 200 includes a blood processing container 14 (see FIG. 3) defining a separation chamber 12 suitable for harvesting mononuclear cells from whole blood. As shown in FIG. 2, a portion of disposable processing set or fluid circuit 200 is mounted on the front panel of device/separator 10. As also shown in FIG. 3, separation chamber 12, which is integral with the rest of circuit 200, is defined by the walls of a flexible processing container 14 carried within an annular gap defined by a rotating spool element 18 and an outer bowl element (not shown) housed within the cabinet of device/separator 10. The processing container 14 takes the form of an elongated tube or belt which is wrapped about the spool element 18 before use. The bowl and spool element 18 are pivoted on a yoke between an upright position and a suspended position, also not shown. In operation, the centrifuge device within separator 10 rotates the suspended bowl and spool element 18 about an axis, creating a centrifugal field within the processing chamber of container 14. Details of the mechanism for causing relative movement of the spool 18 and bowl elements as just described are disclosed in U.S. Pat. No. 5,360,542 entitled "Centrifuge with Separable Bowl and Spool Elements Providing Access to the Separation Chamber," which is also incorporated herein by reference.

With reference to FIGS. 2-3, fluid circuit 200 includes a plurality of processing fluid flow cassettes 23L, 23M and 23R with tubing loops for association with peristaltic pumps 24 on device 10. As described in U.S. Pat. No. 6,027,657, previously incorporated by reference, cassettes 23L, 23M and 23R include molded plastic bodies with integrally molded liquid flow channels. Valve stations (not shown) are molded into the backside of cassette bodies. A flexible diaphragm covers and seals the backside of the cassette (23) body. Valve stations align with valve actuators of pump stations (PSL, PSM and PSR) located on the front panel of device 10. Fluid circuit 200 also includes a network of tubing and pre-connected containers for establishing flow communication with the patient and for processing and collecting fluids and blood and blood components, as shown in greater detail in FIG. 2.

As further seen in FIGS. 2 and 3, in one embodiment disposable processing set 200 may include a container 60 for supplying anticoagulant, a waste container 62 for collecting waste from one or more steps in the process for collecting, treating and/or washing mononuclear cells, a container 64 for holding saline or other priming or conditioning medium, a container 66 for collecting plasma, a container 68 for collecting the mononuclear cells and, as described below, for holding the mononuclear cells during treatment. In one embodiment, a container or pouch 69 for holding the photoactivating agent may be joined to container 68. As shown in FIG. 3, container 69 may be integrally pre-attached to treatment container 68 and in openable fluid communication therewith. A frangible cannula (not shown) may be included in flow path between containers 68 and 69 and broken by the operator to combine the photoactive agent with the collected MNCs in container 68. Alternatively, the portion of the flow path between containers 68 and 69 may be mounted onto automated cannula breaker (not shown) described in greater detail in U.S. Patent Application Publication Nos. US 2014/0263529 and US 2018/0078694, both of which were previously incorporated by reference. Cannula breaker may be activated to open flow path 73 by operator control or by a pre-programmed command received from the system controller (described below) at a pre-determined time. For example, once weight scale 83 holding container 68 detects that a suitable volume of MNCs has been collected, controller 300 may affect breakage of cannula 71, thereby establishing flow from container 69 to container 68.

Alternatively, the photoactivating agent may be delivered directly to container 68 by a syringe through a port in container 68. As noted above, preferably, container 68 also serves as the illumination container, and is preferably pre-attached to the disposable circuit 200. Alternatively, container 68 may be attached to set 200 by known sterile connection techniques, such as sterile docking or the like.

With reference to FIG. 3, fluid circuit includes inlet line 72, an anticoagulant (AC) line 74 for delivering AC from container 60, an RBC line 76 for conveying red blood cells from chamber 12 of container 14 to container 67, a platelet-poor plasma (PPP) line 78 for conveying PPP to container 66 and line 80 for conveying mononuclear cells to and from separation chamber 14 and collection/illumination container 68. The fluid processing circuit includes one or more patient access device(s) such as venipuncture needle(s) for accessing the circulatory system of the patient. As shown in FIG. 3, fluid circuit 200 includes inlet needle 70 and return needle 82. In an alternative embodiment, a single needle can serve as both the inlet and outlet needle.

Container 68 is suitable for irradiation by light of a selected wavelength. By "suitable for irradiation" it is meant that the walls of the container are sufficiently transparent to light of the selected wavelength to activate the photoactive agent. In treatments using UVA light, for example, container walls made of ethylene vinyl acetate (EVA) are suitable. Container 68 may be placed inside irradiation unit 20 by the operator or, more preferably, may be placed inside the irradiation chamber of irradiation device 20 at the beginning of the ECP procedure and prior to whole blood withdrawal (as shown by the broken lines representing device 20 in FIG. 2). In any event, container 68 preferably remains integrally connected to the remainder of fluid circuit 200 during the entire procedure, thereby maintaining the closed or functionally closed condition of fluid circuit 200. After irradiation in device 20 is complete, container 68 may be removed from device 20 and suspended from a weight scale 83 of separator 10.

Figure 6:
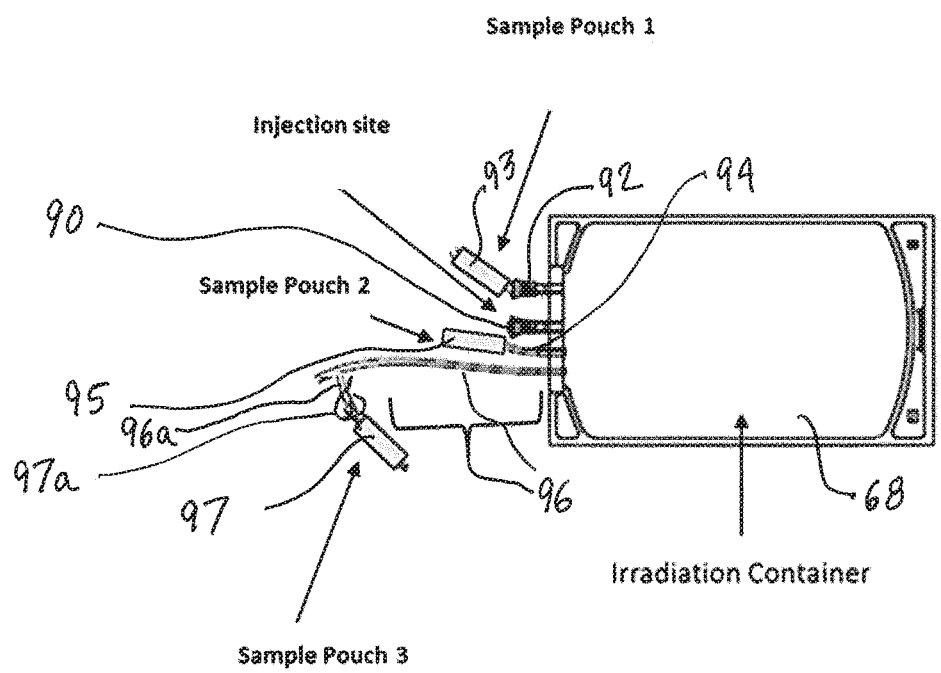
FIG. 6 is a plan view of a treatment container with a plurality of sampling sites for collecting samples at selected times during a photopheresis procedure.

As shown in FIG. 6, and more particularly where the photoactivating agent is delivered to the MNCs by syringe, container 68 includes an injection site 90 through which the 8-MOP or other photoactivating agent is introduced. In addition and in accordance with the present disclosure, container 68 may include a plurality of integral sample sites/pouches for collecting samples at selected times during the course of the photopheresis (ECP) procedure. For example, as shown in FIG. 6, a first sample site, includes a pouch 93 joined to tube 92 at one end of container 68. Additional pouches (e.g., 95 and 97) may be similarly attached in a sterile fashion to respective tubes 94 and 96 which provide a flow path between the interior chamber of container 68 and the pouch (93, 95, 97). Tubes 92, 94 and 96 define flow paths between the interior of container 68 and pouches 93, 95 and 97. Tubes 92, 94 and 96 are preferably sealed by clamps (such as clamp 97a) that are individually opened at the desired time of sampling. Clamps may be traditional, manually operated clamps such as Roberts-type clamps known to those of skill in the art.

By providing a plurality of pouches, samples may be collected at different times of the photopheresis procedure. For example, a sample of the collected blood component, such as MNC, may be collected in pouch 93 prior to introduction of the photoactivating agent into container 68. A second sample may be collected in pouch 95 after the photoactivating agent has been combined with the blood component. A third sample may be collected in pouch 97 after treatment e.g., irradiation of the blood component with light has occurred. Additional pouches and tubes may also be provided. After collection of the sample in any one of pouches 93 and 95 (first and second samples), the tubing 92 and 94 is (heat) sealed and severed prior to placement of container 68 within the irradiation chamber. In one embodiment, the system under the direction of the controller (described below) may prompt the operator to seal and sever sample pouches 93 and 95 at a selected time prior to irradiation. Of course, if no pre-irradiation samples are desired or required, sample pouches may simply be sealed without introducing any samples into pouches 93 and/or 95.

On the other hand, pouch 97 may remain attached to container 68 during irradiation/treatment, albeit preferably located outside of the irradiation chamber. After treatment, a selected volume of the treated blood product is expressed through line 96 and into pouch 97. Afterwards, tube 96 may likewise be sealed and severed and the contents of pouch 97 can be used for further analysis. Samples may be collected at any desired time of the photopheresis procedure including, as described above, post-irradiation and during return of the treated blood component to the patient 100.

Fluid flow through fluid circuit 200 is preferably driven, controlled and adjusted by a microprocessor-based controller in cooperation with the valves, pumps, weight scales and sensors of device 10, the details of which are described in the previously mentioned U.S. Pat. No. 6,027,657. As described below, the controller is programmed to activate rotation of pumps (and control the rotational speed thereof), associated with cassettes 23L, 23M and 23R, open and close valves, receive output signals from sensors and detectors, such as the interface detection system described below, and preferably, to commence and control treatment of the MNC in irradiation unit 20.

Figure 5:
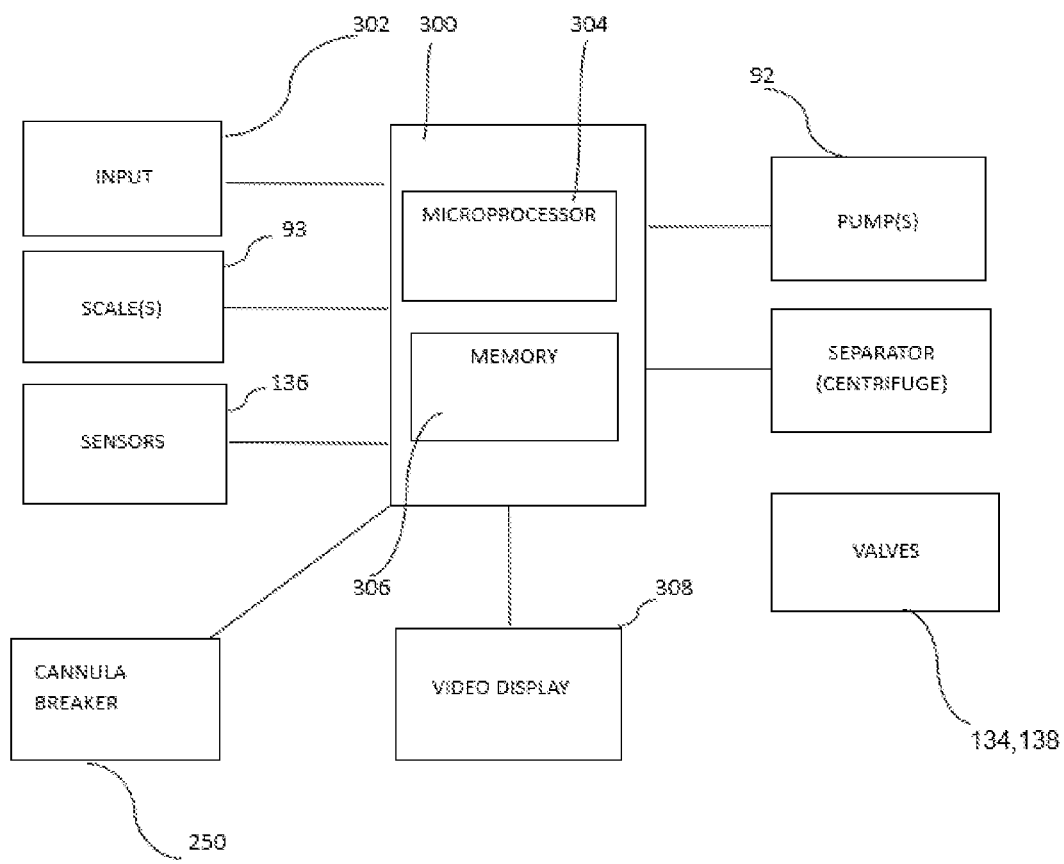
FIG. 5 is a schematic view of the control circuitry, including the controller of the system of FIG. 1.

FIG. 5 is a schematic view of the control unit or "controller" 300 included in device 10 of the present disclosure. The controller 300 may include a microprocessor 304 (which may include multiple physical and/or virtual processors). According to other embodiments, the controller 300 may include one or more electrical circuits designed to carry out the actions described herein. In an embodiment, controller 300 may include a microprocessor and other circuits or circuitry. In addition, the controller 300 may include one or more memories 306. The instructions by which the microprocessor 304 is programmed may be stored on the memory 306 associated with the microprocessor 304, which memory/memories 306 may include one or more tangible non-transitory computer readable memories, having computer executable instructions stored thereon, which when executed by the microprocessor 304, may cause the microprocessors 304 to carry out one or more actions as described herein.

As also illustrated in FIG. 5, controller 300 may be coupled to one or more of the structures described herein, for example to receive information (e.g., in the form of signals) from these structures or to provide commands (e.g., in the form of signals) to these structures to control the operation of the structures. As illustrated in FIG. 5, the controller 300 may be coupled to weight scales 83a-e (seen in FIG. 3) that hold solution containers or containers that are provided to collect or hold separated blood components, the sensors associated with device 10, or more specifically with the cassettes 24L, 24M, and 24R, the valve assemblies 132, and the at least one input 302 to receive information from those devices. Additionally, the controller 300 may be coupled to the pumps 24 and the separator (centrifuge) drive unit (not shown) to provide commands to those devices and to control their operation. As further shown in FIG. 5, controller 300 may also be coupled to automated cannula breaker 250. It may also be possible that the controller 300 receives information from and provides commands to a given structure, such as one of the structures already mentioned. The controller 300 may be directly electrically connected to these structures to be coupled to them, or the controller 300 may be directly connected to other intermediate equipment that is directly connected to these structures to be coupled to them.

The at least one input 302 may include a number of different devices according to the embodiments described herein. For example, the input 302 could include a keyboard or keypad by which a user may provide information and/or instructions to the controller 300. Alternatively, the input 302 may be a touch screen, such as may be used in conjunction with a video display 308 (FIG. 1) that is disposed on the front panel of the device 10, the video display 308 also being coupled to the controller 300. The assembly of the input/touch screen 302 and video display 308 may be one of the aforementioned structures to which the controller 300 is coupled from which the controller 300 receives information and to which the controller 300 provides commands.

In accordance with the present disclosure, controller 300 may be pre-programmed to alert the operator to draw a sample at (a) selected times. For example, during the photopheresis procedure, when a desired volume of MNCs has been collected, as determined by the weight of container 68, a weight scale 83 (for example, 83a) sends a signal to controller 300. Controller 300 may automatically pause further collection to allow the operator to collect a sample in pouch 93, for example. Controller may then prompt the system to proceed with the photopheresis procedure. Controller 300 may also be programmed to prompt the operator to draw a sample into pouch 95 after addition of the photoactivating agent but before irradiation. Finally, controller 300 may be programmed to prompt the operator to draw a sample of the treated MNC product into pouch 97 after treatment by radiation.

For example, once the irradiation treatment has been completed, container 68 may be removed from irradiation device 20 and hung from one of weight scales 83 (and preferably one of weight scales 83b or 83c). Detection of a predetermined weight (e.g. 200g) serves as an indication that the treated MNC product is ready for reinfusion to the patient and that, if desired, a post-treatment sample may be collected.

The controller 300 will pause the reinfusion of the treated MNC to the patient to allow for collection of the "post-sample." Prior to collection of a sample in pouch 97, any fluid remaining in flow path 96 is preferably flushed out. Thus, controller 300 may be pre-programmed to flush a volume equivalent or equal to the volume of flow path 96 before opening (by unclamping clamp 97a on flow path 96a) and establishing fluid communication between the contents of container 68 (post-treatment) and pouch 97. Flushing fluid from flow path 96 prior to collecting a sample in pouch 97 ensures that the collected sample is not further diluted by saline and/or plasma remaining in the flow path from earlier dilution/conditioning steps. Once the desired volume of the treated blood component has been transferred (e.g., by gravity draining) to pouch 97 and the line 96a is resealed, controller 300 will resume return of the treated blood component to the patient.

OTHER ASPECTS

Aspect 1. A method for collecting blood samples in a photopheresis procedure including; programming a photopheresis system for pausing a photopheresis procedure to allow for the collection of blood sample at selected time intervals; collecting a first sample of a blood component to be treated by radiation at a time prior to irradiation of said blood component; continuing with said photopheresis procedure; and collecting a sample of a blood component that has been treated by radiation.

Aspect 2. The method of Aspect 1 further including collecting a sample of a blood component to be treated by radiation at a time prior to irradiation of said blood component but after addition of a photochemical agent.

Aspect 3. The method of any one of Aspects 1 or 2 including pausing the photopheresis procedure at the time of collecting the first sample.

Aspect 4. The method of Aspect 3 including pausing the photopheresis procedure at the time of collecting the sample that has been treated by radiation.

Aspect 5. The method of any one of Aspects 1 through 5 including collecting samples of blood component that is to be treated and has been treated in an treatment container.

Aspect 6. The method of Aspect 6 wherein the irradiation container includes a plurality of sampling sites integrally joined to said treatment container.

Aspect 7. The method of any one of Aspects 5 through 6 including sealing and removing one or more sample pouches from the sample sites in a sterile manner.

Aspect 8. The method of any one of Aspects 5 through 7 wherein a sample site for collecting a sample of an irradiated blood component is integrally joined to said treatment container and is spaced from said container by a tube defining a flow path.

Aspect 9. The method of Aspect 8 comprising flushing said flow path to deliver said treated blood component to the sampling site for collecting a sample of an irradiated blood component.

Aspect 10. The method of any one of Aspects 1 through 9 including determining the amount of said blood component in said treatment container.

Aspect 11. The method of Aspect 10 including determining said amount of said blood component by weighing said treatment container.

Aspect 12. The method of any one of Aspects 10 through 11 including determining said amount of said treated blood component.

Aspect 13. The method of any one of Aspects 1 through 12 further including programming said photopheresis system to alert an operator to collect said samples.

Aspect 14. A system for performing a photopheresis procedure comprising: a separator for separating a target cell population from blood; an illumination device for treating said target cell population with light; a fluid circuit including a treatment container integrally connected to one or more sample pouches; and a controller configured to effect the collection of a sample of said treated target cell population.

Aspect 15. The system of Aspect 14 wherein said controller is further configured to flush a predetermined volume of fluid in said fluid circuit to bypass a sample pouch prior to collecting said sample of said treatment target cell population.

It will be understood that the embodiments described above are illustrative of some of the applications of the principles of the present subject matter. Numerous modifications may be made by those skilled in the art without departing from the spirit and scope of the subject matter disclosed herein, including those combinations of features that are individually disclosed or claimed herein. For the reasons, the scope hereof is not limited to the above description.

The invention claimed is:

1. A system for performing a photopheresis procedure comprising:
   a) a separator for separating a target cell population from blood, said separator comprising a separation device configured to receive a separation chamber;
   b) an illumination device for treating said target cell population with light, said illumination device comprising an irradiation chamber wherein said irradiation chamber is configured to receive a treatment container;
   c) a fluid circuit mounted on the separator, said fluid circuit including said treatment container, said treatment container integrally connected to one or more sample pouches, wherein the one or more sample pouches comprises a first sample pouch for collecting a sample prior to addition of a photoactivating agent, a second sample pouch for collecting a sample after addition of said photoactivating agent but prior to irradiation, and a third sample pouch for collecting a sample after irradiation; and
   d) a controller coupled to the separator and illumination device, wherein the controller is configured to pause said photopheresis procedure and allow for the collection of a sample of said target cell population in one or more of said first, second and third sample pouches respectively at one or more of (1) prior to addition of the photoactivating agent to said target cell population, (2) after addition of said photoactivating agent to but prior to irradiation of said target cell population and (3) after irradiation of said target cell population.

2. The system of claim 1 wherein said controller is further configured to flush a predetermined volume of fluid in said fluid circuit to bypass said third sample pouch for collecting said sample after said irradiation prior to said collecting said sample of said target cell population that has been irradiated.

3. The system of claim 1 wherein said controller is further configured to alert an operator when the sample is to be collected in any one of said first, second and third sample pouches.

4. The system of claim 3 wherein said controller is further configured to pause said photopheresis procedure when the sample is to be collected in any one of said first, second and third sample pouches.

5. The system of claim 2 wherein said predetermined volume is equivalent to a volume of a flow path between said treatment container and said third pouch.

6. The system of claim 1 comprising said irradiation chamber for receiving said treatment container wherein said system is configured such that said one or more integrally connected first, second and thirds sample pouches remain outside of said irradiation chamber during irradiation.

* * * * *